United States Patent [19]

Gunn et al.

[11] Patent Number: 4,761,403

[45] Date of Patent: Aug. 2, 1988

[54] LIPOXYGENASE INHIBITING COMPOUNDS

[75] Inventors: Bruce P. Gunn, Island Lake; James B. Summers, Jr., Libertyville, both of Ill.

[73] Assignee: Abbott Laboratories, North Chicago, Ill.

[21] Appl. No.: 849,924

[22] Filed: Apr. 9, 1986

[51] Int. Cl.$^4$ .................. A61K 31/695; C07F 7/10
[52] U.S. Cl. ..................... 514/63; 514/290; 514/298; 514/309; 514/312; 546/14; 546/101; 546/108; 546/110; 546/142; 546/155
[58] Field of Search ............. 546/14, 142, 155, 101, 546/108, 110; 514/63, 290, 298, 309, 312

[56] References Cited

U.S. PATENT DOCUMENTS

| | | | |
|---|---|---|---|
| 3,455,931 | 7/1969 | Leov | 546/152 |
| 4,393,075 | 7/1963 | Terao et al. | 260/396 R |

FOREIGN PATENT DOCUMENTS

| | | | |
|---|---|---|---|
| 121806 | 10/1974 | European Pat. Off. | 546/121 |
| 104468 | 4/1981 | European Pat. Off. | 548/250 |
| 30861 | 6/1981 | European Pat. Off. | 546/142 |
| 3417573 | 11/1984 | Fed. Rep. of Germany | 546/155 |

OTHER PUBLICATIONS

R. T. Coutts et al., J. Pharm. Sci., 1965, 54, 792–795.
Ohta et al., Chem. Pharm. Bull., 1962, 10, 1260–1261.
Coutts, J. Chem. Soc. C., (1969), 713–716.
Moriconi et al., J. Am. Chem. Soc., 1964, 86, 38–46.
Moriconi et al., J. Org. Chem., 1966, 31, 2090–2098.
Moriconi et al., J. Org. Chem., 1963, 28, 2215–2217.
Chatterjea et al., Leibigs Ann. Chem., 1981, 52–57.
Coutts et al., J. Chem. Soc., 1963, 4610–4612.
Coutts et al., J. Chem. Soc., 1961, 5058–5059.
Eisert, Leibigs Ann. Chem., 1969, 725, 37–51.
Bapat et al., Adv. Heter. Chem., 1969, 10, 199–240.
Corey et al., Journal of the American Chemical Society, 106, 1503–1504.
Radmark et al., 110 FEBS Letters (1980), 213–215.
Morris et al., 19 Prostaglandins (1980), 371–383.
Coutts et al., Meeting Abstract 70 Prostaglandins and Leukotrienes '84.
Walker, Journal of Pharmaceutical Pharmacology, vol. 31, 778–780 (1979).
Samuelsson, Angew. Chem. Int. Ed. Engl. 21 (1982), 902–910.
Green, Tetrahedron, 39 (1983), 1687–1721.
Chatterjea et al., J. Indian Chem. Soc., 1962, 59 (5), 707–9, vol. 97, Chem. Abstracts, p. 805, abstract No. 97:182175u (1982).
Hamana et al., Yakugaku Zasshi, 1975, 95 (1), 87–93 (Japan), abstracted at Chemical Abstracts, vol. 83, 1975, p. 808, abstract No. 9743p (1975).
Tirodkar et al., Curr. Sci., 1972, 41 (18), 679–80, abstracted at vol. 77, Chemical Abstracts, p. 391 (1972), abstract No. 164412b.
Hayashi et al., Yakugaku Zasshi, 1977, 97 (9), 1022–33, abstracted in Chem. Abstracts, vol. 88, Abstract 88:44881j (1978).
Clarkson et al., Chem. Biol. Hydroxamic Acids, 1981, abstracted in Chem. Abstracts, vol. 99, Abstract No. 99:2393f (1983).
Liu et al., J. Chin Chem. Soc., 1975, 22 (4), 317–30, abstracted in Chem. Abstracts, vol. 84, Abstract No. 112457v (1975).
Okamoto et al., Chem. Pharm. Bull., 1971, 19 (9), 1809–14, abstracted in Chem. Abstracts, vol. 75, Abstract 140654q (1971).
Coutts et al., Can. Chem. J., 1970, 48 (15), 2393–2396, abstracted in Chem. Abstracts, vol. 73, Abstract 77022y (1970).
Coutts et al., J. Chem. Soc. C., 1969, 16, 2207–12, abstracted in Chem. Abstracts, vol. 71, Abstract No. 123844(b) (1969).
Yamazaki et al., Yakugaku Zasshi, 1968, 88 (6), 661–4, abstracted in Chem. Abstracts, vol. 69, Abstract 106501d (1968).
Elji, Sci. Papers Inst. Phys. Chem. Res., 56, No. 4, 290–2 (1962), abstracted in Chem. Abstracts, vol. 59, Abstract 2766c (1962).
Masatomo et al., Chem. Pharm. Bull., 10, 51–4 (1962), abstracted in Chem. Abstracts, vol. 58, Abstract 504b (1962).
Motoyoshi et al., Yakugaku Zasshi, 85 (1), 62–6 (1965), abstracted in Chem. Abstracts, vol. 62, abstract 10409d (1965).
Kametani et al., J. Chem. Soc., 1964, 3856–9, abstracted in Chem. Abstracts, vol. 61, abstract 14636 (1964).

*Primary Examiner*—Robert T. Bond
*Attorney, Agent, or Firm*—Steven F. Weinstock; Martin L. Katz

[57] ABSTRACT

Hydroxy quinol-1-one and quinol-2-one based compounds found to be potent inhibitors of 5-, 12-, and 15-lipoxygenase enzymes.

28 Claims, No Drawings

LIPOXYGENASE INHIBITING COMPOUNDS

TECHNICAL FIELD

This invention relates to organic compounds which inhibit lipoxygenase enzymes. It also relates to methods of making such compounds, and to methods of inhibiting lipoxygenase enzymes in human and animal hosts in need of such treatment.

The lipoxygenases are a family of enzymes which catalyze the oxygenation of arachidonic acid. The enzyme 5-lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of mediators, the leukotrienes (LTs). Similarly 12- and 15-lipoxygenase, convert arachidonic acid to 12- and 15-HPETE respectively. Biochemical reduction of 12-HPETE leads to 12-HETE, while 15-HPETE is the precursor of the class of biological agents known as the lipoxins.

A variety of biological effects are associated with these products from lipoxygenase metabolism of arachidonic acid and they have been implicated as mediators in various disease states. For example, the LTs C4 and D4 are potent constrictors of human airways in vitro and aerosol administration of these substances to non-asthmatic volunteers induces broncho constriction. LTB4 and 5-HETE are potent chemotactic factors for inflammatory cells such as polymorphonuclear leukocytes. They also have been found in the synovial fluid of rheumatoid arthritic patients. The biological activity of the LTs has been reviewed by Lewis and Austin (*J. Clinical Invest.* 73, 889, 1984) and by Sirois (*Adv. Lipid Res.* 21, 78, 1985).

The product 12-HETE has been found in high levels in epidermal tissue of patients with psoriasis. The lipoxins have recently been shown to stimulate elastase and superoxide ion release from neutrophils.

Thus, lipoxygenase enzymes play an important role in the biosynthesis of mediators of asthma, allergy, arthritis, psoriasis, and inflammation. Blocking these enzymes interrupts the biochemical pathways involved in these disease states.

BACKGROUND ART

Relatively few compounds are known from the prior art which are inhibitors of the lipoxygenase enzymes. Among the lipoxygenase inhibitors known to the art are: AA-861, a 5-lipoxygenase inhibitor, disclosed in U.S. Pat. No. 4,393,075, issued July 12, 1983 to Terao et al.; pyrazolo pyridines, which are 5-lipoxygenase inhibitors, disclosed in European Patent Application of Irikura et al., Ser. No. 121,806, published Oct. 17, 1984; arachidonyl hydroxamic acid, a 5-lipoxygenase inhibitor, disclosed in E. J. Corey et al., *J. Am. Chem. Soc.*, 106, 1503 (1984) and European Patent Application of P. H. Nelson, Ser. No. 104,468, published Apr. 4, 1984; BW755C, inhibitor of 5- and 12-lipoxygenases, disclosed in Radmark et al., FEBS Lett., 110, 213 (1980); nordihydroguariaretic acid; an inhibitor of 5- and 15-lipoxygenases, disclosed in Morris et al., *Prostaglandins*, 19, (1980); REV-5901, a 5-lipoxygenase inhibitor, disclosed in Coutts, Meeting Abstract 70, *Prostaglandins and Leukotrienes* '84, quinoline N-oxides, 5-lipoxygenase inhibitors disclosed in European patent application of Hashizumo et al., Ser. No. 128,374, published Dec. 19, 1984 and benoxaprofen, disclosed in J. Walker, *Pharm. Pharmacol.*, 31, 778 (1979). It would be useful to have compounds which are more potent inhibitors of these enzymes.

In addition a number of compounds identified as having some lipoxygenase inhibitory activity are structurally related to arachidonic acid. Such compounds are highly susceptible to oxidation in vitro and to breakdown by conventional pathways of lipid metabolism in vivo. Thus as well as having the desired potency it would be desirable to have agents which are relatively simple in structure, and relatively resistant to oxidation and metabolism.

It is an object of the present invention to provide compounds which are highly potent inhibitors of lipoxygenase enzymes.

It is another object of this invention to provide compounds having structures which are simpler and more stable than prior art compounds having lipid-like structures.

It is yet another object of this invention to provide compounds which inhibit lipoxygenase activity in vivo.

These and other objects of this invention will be evident from the following disclosure.

DISCLOSURE OF THE INVENTION

The present invention provides for compounds and methods of using compounds of the formulae I and II in inhibiting lipoxygenase enzyme activity:

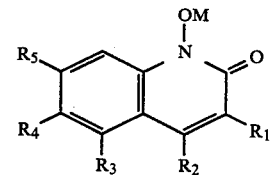

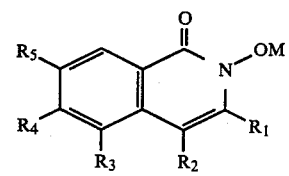

where $R_1$ through $R_5$ are independently selected from hydrogen, $C_1$–$C_{12}$ alkyl, alkoxy, carboalkoxy, aryl, nitro, hydroxy, halogen; or where $R_1$–$R_2$, $R_3$–$R_4$, $R_4$–$R_5$ form an aromatic fused ring; and where M is a pharmaceutically acceptable cation, $C_1$–$C_{12}$ alkyl, acyl, or trialkyl silyl.

The term alkyl is used herein to mean straight and branched chain radicals, including, but not limited to methyl, ethyl, n-propyl, isopropyl, n-butyl, sec-butyl, isobutyl, tert-butyl, and the like.

The term alkoxy is used herein to mean straight and branched chained oxygen ether radicals, including, but not limited to methoxy, ethoxy, isopropoxy, n-butoxy, sec-butoxy, isobutoxy, tert-butoxy, and the like.

The term carboalkoxy is used herein to mean straight or branched chain ester radicals appended at the carbonyl carbon, including, but not limited to carbomethoxy, carboethoxy, carboisopropoxy, carbo-tert-butoxy and the like.

The term acyl is used herein to mean straight or branched chain carbonyl radicals, including but not limited to, formyl, acetyl, propionyl, butyryl, isobutyryl and the like.

The term aryl is used herein to mean substituted and unsubstituted aromatic radicals, including, but not limited to phenyl, 1-napthyl, 2-napthyl and the like.

The term aromatic fused ring is used herein to mean substituted and unsubstituted benzene rings fused to the carbon skeleton of I or II.

The term "pharmaceutically acceptable cation" is used herein to mean hydrogen and the nontoxic cations based on the alkali and alkaline earth metals, such as sodium, lithium, potassium, magnesium, and the like, as well as those based on nontoxic ammonium, quaternary ammonium, and amine cations, including, but not limited to, ammonium, tetramethylammonium, tetraethylammonium, methyl amine, dimethyl amine, trimethyl amine, triethyl amine, ethyl amine, and the like.

METHOD OF TREATMENT

This invention also provides a method of treatment of inhibiting 5-, 12- and/or 15-lipoxygenase activity in a human or lower animal host in need of such treatment which method comprises administration to the human or lower animal host an amount of a compound of this invention effective to inhibit lipoxygenase activity in the host. The compounds of the present invention may be administered orally, parenterally or topically in dosage unit formulations containing conventional nontoxic pharmaceutically acceptable carriers, adjuvants and vehicles as desired.

The term parenteral as used herein includes subcutaneous, intravenous, intramuscular, intrathecal, intraarticular, epidural and intraarterial injection or infusion techniques, without limitation. The term "topically" encompasses administration rectally and by inhalation spray, as well as by the more common routes of the skin and the mucous membranes of the mouth and nose.

Total daily dose of the compounds of this invention administered to a host in single or divided doses may be in amounts, for example, of from 0.001 to 100 mg/kg body weight daily and more usually 0.01 to 10 mg/kg/day. Dosage unit compositions may contain such amounts or such submultiples thereof as may be used to make up the daily dose. It will be understood, however, that the specific dose level for any particular patient will depend upon a variety of factors including the activity of the specific compound employed, the age, body weight, general health, sex, diet, time and route of administration, rates of absorption and excretion, combination with other drugs and the severity of the particular disease being treated.

FORMULATION OF PHARMACEUTICAL COMPOSITIONS

This invention also provides for compositions in unit dosage form for the inhibition of 5-, 12-, or 15-lipoxygenase activity in a human or lower animal host in need of such treatment, comprising a compound of this invention and one or more nontoxic pharmaceutically acceptable carriers, adjuvants or vehicles. The amount of active ingredient that may be combined with such materials to produce a single dosage form will vary depending upon various factors, as indicated above.

A variety of materials can be used as carriers, adjuvants and vehicles in the compositions of this invention, as available in the pharmaceutical arts. Injectable preparations, such as sterile injectable aqueous or oleaginous solutions, suspensions or emulsions, may be formulated according to known art, using suitable dispersing or wetting agents and suspending agents, as needed. The sterile injectable preparation may employ a nontoxic parenterally acceptable diluent or solvent as, for example, sterile, nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils are conventionally employed as solvents or suspending media. For this purpose any bland fixed oil may be used, including synthetic mono-, di- or triglycerides. Fatty acids such as oleic acid can also be used in the preparation of injectable compositions.

Suppositories for rectal administration of the compounds of this invention can be prepared by mixing the drug with suitable nonirritating excipients such as cocoa butter and polyethylene glycols, which are solid at ordinary temperatures but liquid at body temperature and which therefore melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying suspending, sweetening, flavoring and perfuming agents.

SYNTHESIS OF THE COMPOUNDS

Compounds of this invention having formula I can be prepared according to the reaction sequence A below. Although the sequence illustrates the compound where R is hydrogen, it will be seen from the examples that other compounds of this invention can be prepared in the same manner using the appropriate starting materials.

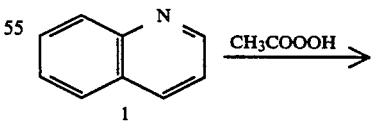

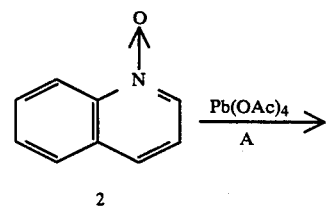

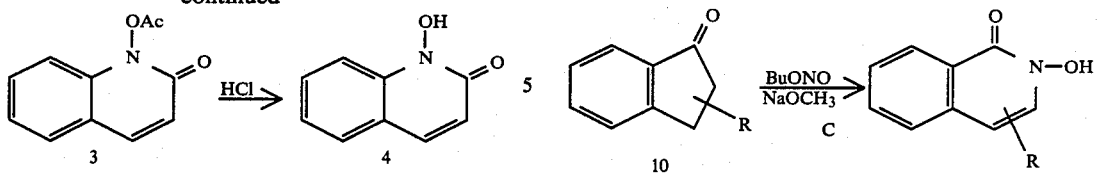

Quinoline (1) is treated with peracetic acid to afford quinoline N-oxide (2) which is treated with lead tetraacetate to yield 1-acetoxyquinol-2(1H)-one (3). The N-hydroxyquinolone (4) is obtained by heating (3) with 2N HCl.

Compounds of this invention having formula II can be prepared according to reaction sequence B below. Although sequence B illustrates the compound where R is hydrogen, it will be seen from the examples that other compounds of this invention can be prepared in the same manner using the appropriate starting materials.

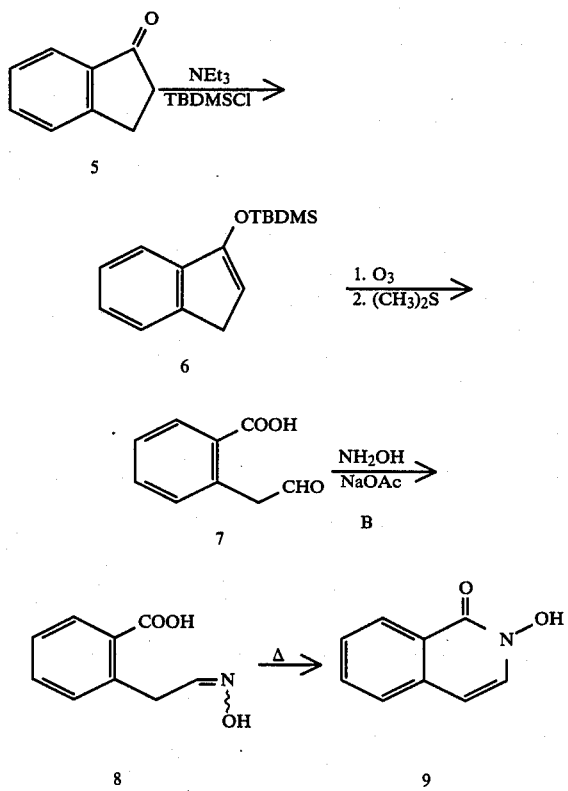

Indanone (5) is converted to its corresponding silyl enol ether (6) with trimethylsilyl chloride or t-butyldimethylsilyl chloride and triethylamine or sodium bis-trimethylsilylamide and t-butyldimethylsilyl chloride. Ozonolysis of (6) followed by a reductive work-up with dimethylsulfide yields the aldehyde acid (7). Reaction with hydroxylamine affords oxime (8) and then heating yields the 2-hydroxyquinol-1(2H)-one (9).

In addition to the method described above, compounds of this invention having formula II where $R_1$ and $R_2$ are other than hydrogen can be prepared according to reaction scheme C below.

Indanone (10) is treated with n-butylnitrite to give 2-hydroxyquinol-1(2H)-one directly.

The following examples further illustrate the synthesis and use of compounds of this invention.

EXAMPLE 1

1-hydroxyquinol-2-(1H)-one

Quinoline N-oxide. Peracetic acid (7.5 mL, 39 mmole, 40%) and quinoline (5 g, 39 mmole) were stirred for 2 hours. Much of the acetic acid was removed from the reaction mixture in vacuo. The resulting residue was dissolved in methylene chloride (50 mL) and washed twice with saturated sodium bicarbonate solution. After drying over MgSO₄ the solvent was evaporated and the residue was triturated with ether. The resulting tan solid was collected by filtration. This material was carried on without further characterization.

1-Hydroxyquinol-2-(1H)-one. The desired material was prepared according to the method of Ochiai and Ohta, *Chem. Abstr.*, 59, 2766, (1963). The crude material prepared as described above (approximately 5.5 g) was dissolved in benzene (100 mL) and CaCO₃ (0.50 g, 5.0 mmole) and lead tetraacetate (20.0 g, 45.1 mmole) were added. The mixture was refluxed for two hours. The lead by-products which precipitated were filtered off and rinsed with methylene chloride. The solvent was evaporated in vacuo to give a very dark oil. Hydrochloric acid (2N, 25 mL) was added and refluxed for 30 minutes. A brown solid formed which was isolated by filtration and recrystallized from benzene.

Melting Point: 188° C.

EXAMPLE 2

3-Carbomethoxy-1-hydroxyquinol-2(1H)-one

Methyl 1-carbomethoxy-3-(2-nitrophenyl)propenoate. The desired material was prepared according to the method described in *J. Chem. Soc.*, 3462 (1960). Dimethyl malonate (5.28 g, 40 mmole), acetic anhydride (15.08 mL, 160 mL), sodium bicarbonate (5.04 g, 40 mmole), and 2-nitrobenzaldehyde were heated at 100° C. for 2 hrs. After cooling, the mixture was diluted with water, extracted into ether and washed with saturated sodium bicarbonate. The solvent was removed in vacuo and the residue chromatographed, eluting with 45% ether in pentane. A yellow oil (2.7 g) was obtained. It crystallized on standing.

3-Carbomethoxy-1-hydroxyquinol-2(1H)-one. The desired material was prepared according to the method found in *J. Chem. Soc. C*, 713, (1969). To a water solution (20 mL) of sodium borohydride (0.75 g, 20 mmole) and 10% palladium on charcoal (0.075 g) was added a methanol solution (20 mL) of the diester prepared as above (2.7 g, 10 mmole). The mixture was stirred at room temperature for thirty minutes and then filtered. The filtrate was acidified with concentrated HCl and the solid which formed was recrystallized from water to afford 700 mg of fine needles.

Melting Point: 170°-171° C.

IR (KBr): 3450, 1740, 1708, 1625, 1580, 1304, 792, 755.

Mass Spectrum: 219 (M+), 203, 187, 172, 143, 115.

EXAMPLE 3

3-Bromo-1-hydroxyquinol-2-(1H)-one

Using the method of Example 1, but using 3-bromoquinoline, the desired compound was obtained.

Melting Point: 185°–186° C.

IR (KBr): 3070(br), 1620(s), 1580(s).

Mass Spectrum: 239, 241 (M+); 225, 223, 196, 194.

EXAMPLE 4

4-Methyl-1-hydroxyquinol-2(1H)-one

Using the method of Example 1, but using 4-methylquinoline the desired compound was obtained.

Melting Point: 187° C.

IR (KBr): 1640, 1612, 1590, 970, 780.

Mass Spectrum: 161 (M+), 134, 116, 105.

EXAMPLE 5

4-Chloro-6-methoxy-1-hydroxyquinol-2(1H)-one

Using the method of Example 1, but using 4-chloro-6-methoxyquinoline, the desired compound was obtained.

Melting Point: 210°–215° C. (dec).

NMR (DMSO-$d_6$): 3.92 (s, 3H), 7.03 (s, 1H), 7.29–7.41 (m, 3H).

Mass Spectrum: 225, 227 (M+), 210, 208, 201, 180.

EXAMPLE 6

5-Nitro-1-hydroxyquinol-2(1H)-one

Using the method of Example 1, but using 5-nitroquinoline, the desired compound was obtained.

Melting Point: 205° C. (sublime).

NMR (DMSO-$d_6$): 6.96 (d, 1H), 7.84 (t, 1H), 7.97 (d, 1H), 8.03 (d, 1H), 8.23 (d, 1H), 11.83 (s, 1H).

Mass Spectrum: 206 (M+), 190, 174, 160, 130, 115.

EXAMPLE 7

6-Methyl-5-nitro-1-hydroxyquinol-2(1H)-one

Using the method of Example 1, but using 6-methyl-5-nitroquinoline, the desired compound was obtained.

Melting Point: 230° C. (dec).

NMR (DMSO-$d_6$): 2.35 (s, 3H), 6.87 (d, 1H) 7.65–7.88 (m, 3H), 11.76 (s, 1H).

Mass Spectrum: 220 (M+), 203, 186, 175, 157, 145, 128, 115.

EXAMPLE 8

6-Chloro-1-hydroxyquinol-2(1H)-one

Using the method of Example 1, but using 6-chloroquinoline the desired compound was obtained.

Melting Point: 175°–177° C.

IR (KBr): 1640, 1625, 1420, 820, 812.

Mass Spectrum: 195, 197 (M+); 178, 150, 138, 123, 114

EXAMPLE 9

6-Methyl-1-hydroxyquinol-2-(1H)-one

Using the method of Example 1, but using 6-methylquinoline, the desired compound was obtained.

Melting Point: 201°–202° C.

IR (KBr): 3050(br); 1625(br,s); 1580(br,s).

Mass Spectrum: 175 (M+), 158, 146, 130, 118, 103.

EXAMPLE 10

6-Methoxy-1-hydroxyquinol-2-(1H)-one

Using the method of Example 1, but using 6-methoxyquinoline, the desired compound was obtained.

Melting point: 193°–194° C.

NMR (CDCl$_3$): 3.80 (s, 3H), 6.72 (d, 1H, J=9 Hz), 7.30 (m, 2H), 7.62 (d, 1H, J=9 Hz), 7.85 (d, 1H, J=9 Hz).

IR (KBr): 1630, 1573, 1250, 1163, 830.

Mass Spectrum: 191(M+), 174, 146, 132, 120, 103.

EXAMPLE 11

6-Nitro-1-hydroxyquinol-2(1H)-one

Using the method of Example 1, but using 6-nitroquinoline, the desired compound was obtained.

Melting Point: 184°–185° C. (dec).

IR (KBr): 1665, 1620, 1520, 1345, 835.

Mass Spectrum: 206 (M+), 190, 176, 160, 144, 132, 116.

EXAMPLE 12

6-Phenyl-1-hydroxyquinol-2(1H)-one

Using the method of Example 1, but using 6-phenylquinoline, the desired compound was obtained.

Melting Point: 219°–220° C.

IR (KBr): 1670, 1590, 1571, 1425, 818, 759.

Mass Spectrum: 237 (M+), 220, 192, 165, 152.

EXAMPLE 13

7-Methyl-1-hydroxyquinol-2(1H)-one

Using the method of Example 1, but using 7-methylquinoline the desired compound was obtained.

Melting Point: 170°–172°

NMR (DMSO-d6): 2.45 (s, 3H), 6.63 (d, 1H), 7.10 (d, 1H), 7.5 (s, 1H), 7.65 (d, 1H), 7.86 (d, 1H), 11.30 (d, 1H).

IR (KBr): 1640, 1500, 1407, 1163, 855.

Mass Spectrum: 175 (M+), 158, 146, 130, 118, 103.

EXAMPLE 14

5,6-Benzo-1-hydroxyquinol-2(1H)-one

Using the method of Example 1, but using 5,6-benzoquinoline, the desired compound was obtained.

Melting Point: 240° C. dec.

NMR (DMSO-d6): 6.87 (d, 1H), 7.55–8.85 (m, 7H).

Mass Spectrum: 211 (M+), 195, 182, 166, 154, 139, 127.

EXAMPLE 15

3,4-Benzo-1-hydroxyquinol-2(1H)-one

Using the method of Example 1, but using 3,4-benzoquinoline the desired compound was obtained.

Melting Point: 238°–240° C. dec.

IR (KBr): 3050(br); 1625(s); 1604(s); 1590(s).

Mass Spectrum: 211 (M+), 195, 166, 140.

EXAMPLES 16–26

By using the method of Example 1 with the following starting materials, the indicated compounds can be prepared:

| Ex. | Starting Material | Product |
| --- | --- | --- |
| 16 | 3-Isopropylquinoline | 3-Isopropyl-1-hydroxyquinol-2(1H)—one |
| 17 | 3-Phenylquinoline | 3-Phenyl-1-hydroxy- |

-continued

| Ex. | Starting Material | Product |
|---|---|---|
| | | quinol-2(1H)—one |
| 18 | 3-Chloroquinoline | 3-Chloro-1-hydroxy-quinol-2(1H)—one |
| 19 | 4-Ethylquinoline | 4-Ethyl-1-hydroxy-quinol-2(1H)—one |
| 20 | 4-Nitroquinoline | 4-Nitro-1-hydroxy-quinol-2(1H)—one |
| 21 | 5-Methylquinoline | 5-Methyl-1-hydroxy-quinol-2(1H)—one |
| 22 | 5-Methoxyquinoline | 5-Methoxy-1-hydroxy-quinol-2(1H)—one |
| 23 | 6-Carbomethoxyquinoline | 6-Carbomethoxy-1-hydroxyquinol-2(1H)—one |
| 24 | 6,7-Benzoquinoline | 6,7-Benzo-1-hydroxy-quinol-2(1H)—one |
| 25 | 7-Methoxyquinoline | 7-Methoxy-1-hydroxy-quinol-2(1H)—one |
| 26 | 7-Phenylquinoline | 7-Phenyl-1-hydroxy-quinol-2(1H)—one |

EXAMPLE 27

2-hydroxyquinol-1(2H)-one

1-Trimethylsiloxyindene. Trimethylsilyl chloride (5.7 g, 52.3 mmole), triethylamine (11.71 g, 116 mmole), and 1-indanone (6.22 g, 47.1 mmole) were dissolved in dimethyl formamide (25 mL) and refluxed for 17 hours. After cooling, the mixture was diluted with pentane (50 mL) and washed four times with saturated sodium bicarbonate. After backwashing the aqueous phase with pentane the organic layers were combined, washed with cold 2N HCl and cold saturated sodium bicarbonate, then dried over MgSO$_4$. The solvent was evaporated and the residue distilled (bp 123°–125° C.).

NMR (CDCl$_3$): 0.35 (s, 9H); 3.3 (d, 2H, J=2 Hz); 5.45 (t, 1H, J=2 Hz); 7.2–7.6 (m, 4H).

(2-Carboxyphenyl)acetaldehyde. Ozone was bubbled through a methanol solution (25 mL) of the silyl enol ether prepared above (1 g, 4.9 mmole) at −78°. After five minutes the reaction turned blue indicating the end of the reaction. After purging with nitrogen, the reaction was quenched with dimethylsulfide (1 g, 16.1 mmole) and stirred for two hours at 0°. The solvent was evaporated and the residue chromatographed (eluting with ether/hexane) to afford 0.5 g of a white solid.

NMR (CDCl$_3$): 3.2 (d, 2H, J=4 Hz), 5.9 (t, 1H, J=4 Hz), 7.0–8.2 (m, 4H).

Mass Spectrum: 165, 164 (M+), 147, 136, 118, 90.

(2-Carboxyphenyl)acetaldehyde oxime. This step was patterned after the method of Robinson, *J. Am. Chem. Soc.*, 80, 3443 (1958). The material prepared above (350 mg, 2.1 mmole) was suspended in 5 mL water and heated to dissolve. Hydroxylamine (213 mg, 3.1 mmole) and sodium acetate (254 mg, 3.1 mmole) were added and the mixture was heated for 15 minutes. After cooling a solid precipitated which was recrystallized from nitromethane to afford 145 mg of a white solid. This was carried on without characterization.

2-Hydroxy-quinol-1(2H)-one. The material (140 mg, 0.8 mmole) prepared above was dissolved in xylene and heated to 130° for three hours. Upon cooling a yellow solid precipitated which was recrystallized from nitromethane to afford a tan solid (70 mg).

Melting Point: 187°–188° C.

NMR (DMSO-d6): 6.62 (d, 1H), 7.47–7.80 (m, 4H), 8.25 (d, 1H).

IR (KBr): 3100(br), 1640(s), 1612(s), 1585(s), 780.

Mass Spectrum: 161 (M+), 134, 116, 105, 89.1

EXAMPLE 28

2,3-Dihydroxyquinol-1(2H)-one

Sodium carbonate (5.3 g, 0.05 mole) and hydroxylamine hydrochloride (6.95 g, 0.1 mmole) were dissolved in water (30 mL) and the anhydride of 2-carboxyphenylacetic acid (16.21 g, 0.1 mole) was added. The mixture was stirred manually. It became very thick and foamed excessively. More water was added and the mixture was heated on a steam bath. Within 2 minutes the mixture solidified. More water was added and the reaction mixture was filtered. The crude product was recrystallized from ethanol.

Melting Point: 200°–201° C.

EXAMPLE 29

4-Bromo-2-hydroxyquinol-1(2H)-one

The material prepared in Example 27 (1.09 g, 6.8 mmole) was dissolved in acetic acid (15 mL) and bromine (600 mg, 7.5 mmole) was added in 1 mL acetic acid, being careful to maintain the temperature below 30°. The starting material dissolved mid-way through the reaction and then later a new material precipitated. The mixture was diluted with water and the product collected by filtration. Recrystallization from nitromethane afforded fluffy white needles (630 mg).

Melting Point: 197°–199° C.

NMR (DMSO-d6): 7.67–7.93 (m, 3H), 8.17 (s, 1H), 8.3 (d, 1H), 11.85 (s, 1H).

IR (KBr): 1660, 1595, 1470, 765.

Mass Spectrum: 239, 241 (M+); 223, 196, 194, 171, 169.

EXAMPLE 30

4-Nitro-2-hydroxyquinol-1(2H)-one

The material prepared as in Example 27 (620 mg, 3.9 mmole) was dissolved in a mixture of acetic acid (2 mL), sulfuric acid (5 mL), and water (0.5 mL) and cooled to 0° C. Sodium nitrite (800 mg, 11.6 mmole) in water (2 mL) was added being careful to maintain the temperature below 10° C. After stirring for four hours the reaction mixture was diluted with water and a yellow precipitate formed. The solid was filtered, dried, and recrystallized form nitromethane to afford 200 mg.

Melting Point: 163°–165° C. dec.

NMR (DMSO-d6): 7.72 (t, 1H), 7.97 (t, 1H), 8.38 (t, 1H), 8.62 (t, 1H), 9.16 (s, 1H).

Mass Spectrum: 206, 190, 176, 146, 129, 88.

EXAMPLE 31

4-Phenyl-2-hydroxyquinol-1(2)-one

3-Phenyl-1-indanone. The desired material was prepared according to the method of C. F. Koelsch, *J. Am. Chem. Soc.*, 65, 59 (1943). Cinnamic acid (17 g) was dissolved in benzene (75 mL) and aluminum chloride (50 g) was cautiously added. After the initial vigorous reaction had subsided, the mixture was refluxed for five hours. The reaction was quenched by pouring on ice, concentrated HCl was added and the mixture was extracted with benzene. The organic layer was washed with 2N NaOH and distilled water, dried over magnesium sulfate and evaporated in vacuo. The residue was chromatographed on silica gel eluting with 20% ether in pentane to afford 6.5 g of white solid.

Melting Point: 74.5°–75° C.

IR (CDCl₃): 3010, 1708(s), 1602, 1290, 1240.
Mass Spectrum: 208 (M+), 193, 178, 165, 152, 140, 130, 115.

4-Phenyl-2-hydroxyquinol-1(2H)-one. This step was patterned after the method of Chatterjee, *Liebigs Ann. Chem.*, 52 (1981). To methanol (20 mL) under nitrogen at room temperature was added sodium metal (1.08 g, 47 mmole) in small pieces. After the sodium metal had been completely consumed, the excess methanol was removed in vacuo. The resulting sodium methoxide was suspended in ether (50 mL) and cooled to 0° C. under nitrogen with vigorous stirring. An ether solution (15 mL) of butyl nitrate (1.67 mL, 14.3 mmole) and 3-phenyl-1-indanone (prepared above, 2.08 g, 10 mmole) was added dropwise over 10 minutes. After stirring for 5 hours at 0° C., the reaction flask was placed in a freezer (−10° C.) for 16 hours. The cold mixture was then diluted with water (100 mL) and the aqueous layer was separated. The dark water layer was acidified (to litmus) with concentrated HCl. The precipitate which formed was collected and recrystallized from ethanol to afford 320 mg of tan crystals.
Melting Point: 202.5°–204° C.
IR (KBr): 1605, 1495, 1345, 1325, 1170.
Mass Spectrum: 237 (M+), 220, 192, 181, 165.

EXAMPLE 32

4-Methyl-2-hydroxy-quinol-1(2H)-one

Using the method of Example 27, except using 3-methyl-1-indanone, the desired material was obtained.
Melting Point: 207.5°–209° C.
NMR (DMSO-d6): 2.20 (s, 3H), 7.75–7.77 (m, 4H), 8.25 (m, 1H).
IR (KBr): 1640, 1615, 1590, 1500, 1470, 1260.
Mass Spectrum: 175 (M+), 158, 147, 130, 115, 103.

EXAMPLE 33

5-Methyl-2-hydroxyquinol-2(1H)-one

Using the method of Example 27, but using 4-methylindanone, the desired compound was obtained.
Melting Point: 180°–182° C.
Mass Spectrum: 175(M+), 158, 148, 130, 119, 103.

EXAMPLE 34

7-Methoxy-2-hydroxyquinol-2(1H)-one

Using the method of Example 27, but using 6-methoxyindanone, the desired compound was obtained.
Melting Point: 171°–172° C.
NMR (DMSO-d₆): 3.88 (s, 3H), 6.59 (d, 1H), 7.32–7.68 (m, 4H), 11.52 (s, 1H).
IR (KBr): 1625, 1585, 1250, 1162, 861, 828, 613.
Mass Spectrum: 191(M+), 174, 146, 135, 117, 103.

EXAMPLE 35

3,4-Diphenyl-2-hydroxyquinol-2(1H)-one

Using the method of Example 31, but using 2,3-diphenylindanone, the desired compound was obtained.
NMR (DMSO-d₆): 7.10–7.70 (m, 13H), 8.40 (d, 1H), 11.14 (s, 1H).
Mass Spectrum: 313(M+), 296, 209, 193, 181, 165.

EXAMPLES 36-47

By using the method of Example 27 with the following starting materials, the indicated compounds can be prepared:

| Ex. | Starting Material | Product |
|---|---|---|
| 36 | 2-Pentylindanone | 3-Pentyl-2-hydroxy-quinol-1(2H)-one |
| 37 | 2-Methoxyindanone | 3-Methoxy-2-hydroxy-quinol-1(2H)-one |
| 38 | 3-Methoxyindanone | 4-Methoxy-2-hydroxy-quinol-1(2H)-one |
| 39 | 4-Methoxyindanone | 5-Methoxy-2-hydroxy-quinol-1(2H)-one |
| 40 | 4-Chloroindanone | 5-Chloro-2-hydroxy-quinol-1(2H)-one |
| 41 | 5-Methylindanone | 6-Methyl-2-hydroxy-quinol-1(2H)-one |
| 42 | 5-Methoxyindanone | 6-Methoxy-1-hydroxy-quinol-1(2H)-one |
| 43 | 5-Phenylindanone | 6-Phenyl-2-hydroxy-quinol-1(2H)-one |
| 44 | 5-Bromoindanone | 6-Bromo-2-hydroxy-quinol-1(2H)-one |
| 45 | 6-Methylindanone | 7-Methyl-2-hydroxy-quinol-1(2H)-one |
| 46 | 6-Phenylindanone | 7-Phenyl-2-hydroxy-quinol-1(2H)-one |
| 47 | 6-Bromoindanone | 7-Bromo-2-hydroxy-quinol-1(2H)-one |

Lipoxygenase IC50 Determination

The compounds of this invention are potent inhibitors of 5-, 12-, and 15-lipoxygenases. An assay to determine 5-lipoxygenase activity was performed in incubations containing various concentrations of the test compound and the 20,000 g supernatant from 7.5 million homogenized RBL-1 cells. Reactions were initiated by addition of radiolabeled arachidonic acid and terminated by acidification and ether extraction. Reaction products were separated from nonconverted substrate by thin layer chromatography and measured by liquid scintillation spectroscopy. Inhibition of 5-lipoxygenase activity was calculated as the 50% intercept from linear regression analysis of percentage inhibition versus log concentration plots. Results for compounds of the foregoing examples are indicated in Table 1, below.

TABLE 1

| Example | Formula | Substituent | IC50 (uM) |
|---|---|---|---|
| 1 | I | -none- | 5.3 |
| 2 | I | R1 = carbomethoxy | 24 |
| 3 | I | R1 = bromo | 4.2 |
| 4 | I | R2 = methyl | 1.4 |
| 5 | I | R2 = chloro, R4 = methoxy | 1.6 |
| 6 | I | R3 = nitro | 3.7 |
| 7 | I | R3 = nitro, R4 = methyl | 2.0 |
| 8 | I | R4 = chloro | 0.87 |
| 9 | I | R4 = methyl | 1.1 |
| 10 | I | R4 = methoxy | 1.5 |
| 11 | I | R4 = nitro | 14 |
| 12 | I | R4 = phenyl | 0.34 |
| 13 | I | R5 = methyl | 0.98 |
| 14 | I | R3,R4 = benzo | 0.84 |
| 15 | I/II | R1,R2 = benzo | 2.5 |
| 27 | II | -none- | 6.0 |
| 28 | II | R1 = hydroxyl | 54% @ 100 uM |
| 29 | II | R2 = bromo | 2.6 |
| 30 | II | R2 = nitro | 32% @ 30 uM |
| 31 | II | R2 = phenyl | 0.45 |
| 32 | II | R2 = methyl | 3.9 |
| 33 | II | R3 = methyl | 2.4 |
| 34 | II | R5 = methoxy | 2.5 |
| 35 | II | R1,R2 = phenyl | 1.5 |

Inhibitory activities of the compounds of this invention against 12- and 15-lipoxygenase can be determined in the foregoing assay in which 12-lipoxygenase obtained from human platelets, or 15-lipoxygenase obtained from soybean, is substituted for the 15-lipoxygenase containing cell supernatant fraction. Results of these tests for various of the foregoing compounds are indicated in Table 2.

TABLE 2

| | Percent Inhibition at Indicated Concentration | | | |
|---|---|---|---|---|
| | 12-Lipoxygenase | | 15-lipoxygenase | |
| Example | 100 uM | 10 uM | 100 uM | 10 uM |
| 1 | 98 | 93 | 95 | 59 |
| 2 | 94 | 66 | 14 | 5 |
| 6 | 98 | 83 | 98 | 27 |
| 8 | 97 | 95 | 100 | 95 |
| 10 | 97 | 90 | 94 | 62 |
| 11 | 90 | 67 | 32 | 2 |
| 12 | 98 | 97 | 100 | 97 |
| 13 | 97 | 94 | 97 | 61 |
| 15 | 98 | 96 | 60 | 13 |
| 16 | 98 | 93 | 93 | 40 |
| 29 | 96 | 89 | 94 | 43 |
| 30 | 83 | 54 | 12 | 10 |
| 31 | 99 | 95 | 50 | 14 |
| 34 | 98 | 90 | 45 | 20 |

The foregoing is merely illustrative of the invention and is not intended to limit the invention to the disclosed compounds. Variations and change which are obvious to one skilled in the art are intended to be within the scope and nature of the invention which are defined in the appended claims.

What is claimed is:

1. A method of inhibiting lipoxygenase activity in a human or lower animal in need of such treatment, comprising administering to the human or lower animal a therapeutically effective amount of a compound of the formula I or II

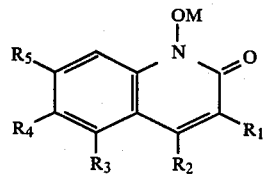

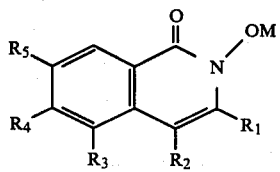

wherein
$R_1$ through $R_5$ are independently selected from hydrogen, $C_1$-$C_{12}$ alkyl, $C_1$-$C_{12}$ alkoxy, $C_1$-$C_8$ carboalkoxy, $C_6$ or $C_{10}$ aryl, nitro, hydroxy, a halogen, or where $R_1$-$R_2$, $R_3$-$R_4$, or $R_4$-$R_5$ form an aromatic fused ring;
and where M is a pharmaceutically acceptable cation, tri-$C_1$-$C_6$ alkylsilyl or $C_1$-$C_{12}$ alkyl or acyl.

2. A compound of the formula

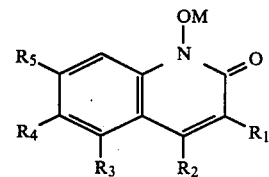

where R1 is selected from chloro, fluoro, iodo, $C_6$ or $C_{10}$ aryl, selected from phenyl, 1-naphthyl and 2-naphthyl; $C_1$-$C_8$ carboalkoxyl, $C_3$-$C_{12}$ alkoxy or $C_5$-$C_{12}$ alkyl; and where R2-R5 independently are selected from hydrogen, $C_1$ to $C_8$ alkyl or $C_1$-$C_8$ alkoxy, aryl, selected from phenyl, 1-naphthyl and 2-naphthyl; halo, nitro, or $C_1$-$C_8$ carboalkoxy; or R1-R2, R3-R4 or R4-R5 independently form an aromatic fused ring, provided that R2-R5 are not all hydrogen when R1 is carboalkoxy and R3-R5 are not all hydrogen when R1-R2 is an aromatic fused ring; M is a pharmaceutically acceptable cation, $C_1$ to $C_{12}$ alkyl or acyl, or trialkylsilyl wherein the alkyl groups have from 1 to 6 carbon atoms.

3. A pharmaceutical composition in unit dosage form, comprising a therapeutically effective amount of a compound according to claim 2 in combination with a pharmaceutical carrier.

4. A method of inhibiting lipoxygenase activity in a human or lower animal in need of such treatment, comprising administering to the human or lower animal a therapeutically effective amount of the composition of claim 2.

5. A compound of the formula

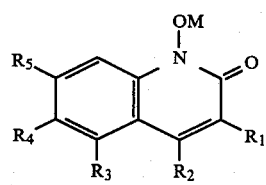

where R1 is alkyl of from 1 to 4 carbon atoms, methoxy or ethoxy and R2-R5 independently are selected from $C_2$-$C_{12}$ aklyl or $C_2$-$C_{12}$ alkoxy, aryl, selected from phenyl, 1-naphthyl and 2-naphthyl; halo, nitro, or $C_1$-$C_8$ carboalkoxy; or where independently R3-R4 or R4-R5 form an aromatic fused ring; M is a pharmaceutically acceptable cation, $C_1$ to $C_{12}$ alkyl or acyl, or trialkylsilyl wherein the alkyl groups have from 1 to 6 carbon atoms.

6. A pharmaceutical composition in unit dosage form, comprising a therapeutically effective amount of a compound according to claim 5 in combination with a pharmaceutical carrier.

7. A method of inhibiting lipoxygenase activity in a human or lower animal in need of such treatment, comprising administering to the human or lower animal a therapeutically effective amount of the composition of claim 5.

8. A compound of the formula

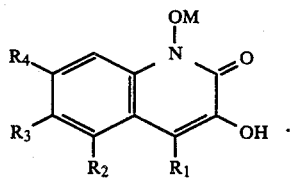

where $R_1$ is selected from $C_3$–$C_{12}$ alkyl, $C_2$–$C_{12}$ alkoxyl, $C_{10}$ aryl selected from 1-naphthyl and 2-naphthyl; halo, nitro, or hydroxy; $R_2$–$R_4$ independently are selected from hydrogen, $C_1$ to $C_8$ alkyl or $C_1$ to $C_8$ alkoxy, $C_6$ or $C_{10}$ aryl selected from phenyl, 1-naphthyl and 2-naphthyl; halo, nitro, hydroxy or $C_1$–$C_8$ carboalkoxy; or where independently $R_2$–$R_3$ or $R_3$–$R_4$ form an aromatic fused ring; M is a pharmaceutically acceptable cation, $C_1$ to $C_{12}$ aklyl or acyl, or trialkylsilyl wherein the alkyl groups have from 1 to 6 carbon atoms.

9. A pharmaceutical composition in unit dosage form, comprising a therapeutically effective amount of a compound according to claim 8 in combination with a pharmaceutical carrier.

10. A method of inhibiting lipoxygenase activity in a human or lower animal in need of such treatment, comprising administering to the human or lower animal a therapeutically effective amount of the composition of claim 8.

11. A compound of the formula:

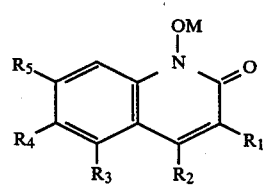

where $R_1$ is bromo or nitro, $R_2$ is selected from $C_1$ to $C_8$ alkyl or $C_1$ to $C_8$ alkyl or $C_1$ to $C_8$ alkoxy, aryl, selected from phenyl, 1-naphthyl and 2-naphthyl; halo, nitro, or $C_1$–$C_8$ carboalkoxy and $R_3$–$R_5$ independently are selected from hydrogen, $C_1$ to $C_8$ alkyl or $C_1$ to $C_8$ alkoxy, aryl, selected from phenyl, 1-naphthyl and 2-naphthyl; halo, nitro, hydroxy, $C_1$–$C_8$ carboalkoxy; or where independently $R_3$–$R_4$ or $R_4$–$R_5$ form a aromatic fused ring; M is a pharmaceutically acceptable cation, $C_1$ to $C_{12}$ alkyl or acyl, or trialkylsilyl wherein the alkyl groups have from 1 to 6 carbon atoms.

12. A pharmaceutical composition in unit dosage form, comprising a therapeutically effective amount of a compound according to claim 11 in combination with a pharmaceutical carrier.

13. A method of inhibiting lipoxygenase activity in a human or lower animal in need of such treatment, comprising administering to the human or lower animal a therapeutically effective amount of the composition of claim 11.

14. A compound of the formula:

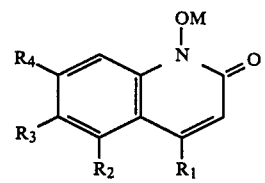

where $R_1$–$R_4$ independently are selected from hydrogen, $C_1$ to $C_8$ aklyl or $C_1$ to $C_8$ alkoxy, aryl, selected from phenyl, 1-naphthyl and 2-naphthyl; halo, nitro, hydroxy or $C_1$–$C_8$ carboalkoxy, provided that:

$R_1$–$R_4$ are not all hydrogen, $R_1$ is not hydroxyl or chloro when $R_2$–$R_4$ are hydrogen, neither $R_2$ nor $R_3$ are nitro when the remainder of $R_1$–$R_4$ are hydrogen, $R_3$ is not bromo when the remainder of $R_1$–$R_4$ are hydrogen, and $R_3$ and $R_4$ are not simultaneously methyl when $R_1$ and $R_2$ are hydrogen;

or where independently $R_2$–$R_3$ or $R_3$–$R_4$ form an aromatic fused ring; M is a pharmaceutically acceptable cation; $C_1$ to $C_{12}$ alkyl or acyl, or trialkylsilyl wherein the alkyl groups have from 1 to 6 carbon atoms.

15. A pharmaceutical composition in unit dosage form, comprising a therapeutically effective amount of a compound according to claim 14 in combination with a pharmaceutical carrier.

16. A method of inhibiting lipoxygenase activity in a human or lower animal in need of such treatment, comprising administering to the human or lower animal a therapeutically effective amount of the composition of claim 14.

17. A compound according to claim 14 wherein $R_3$ is chloro.

18. A compound according to claim 14 wherein $R_3$ is phenyl.

19. A compound of the formula:

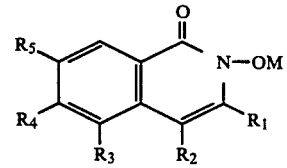

where $R_1$ is selected from $C_5$ to $C_8$ alkoxy or $C_1$ to $C_8$ carboalkoxy or $C_{10}$ aryl selected from 1-naphthyl and 2-naphthyl; halo, nitro, hydroxy; $R_2$–$R_5$ independently are selected from hydrogen, $C_1$ to $C_4$ lower alkyl, $C_1$ to $C_4$ lower alkoxy, aryl selected from phenyl, 1-naphthyl and 2-naphthyl; halo, nitro, or $C_1$–$C_8$ carboalkoxy or $R_1$–$R_2$, $R_3$–$R_4$ or $R_4$–$R_5$ independently form an aromatic fused ring, provided that $R_3$–$R_5$ are not all hydrogen when $R_1$–$R_2$ is an aromatic ring; M is a pharmaceutically acceptable cation, $C_1$ to $C_{12}$ alkyl or acyl, or trialkylsilyl wherein the alkyl groups have from 1 to 6 carbon atoms.

20. A pharmaceutical composition in unit dosage form, comprising a therapeutically effective amount of a compound according to claim 19 in combination with a pharmaceutical carrier.

21. A method of inhibiting lipoxygenase activity in a human or lower animal in need of such treatment, comprising administering to the human or lower animal a therapeutically effective amount of the composition of claim 19.

22. A compound of the formula

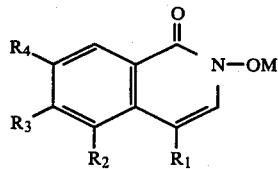

where $R_1$ is selected from hydrogen, $C_2$ to $C_8$ alkyl, $C_1$ to $C_8$ alkoxy or $C_1$ to $C_8$ carboalkoxy, fluoro, chloro, iodo, nitro, hydroxy, or $C_{10}$ aryl selected from 1-naphthyl and 2-naphthyl; $R_2$–$R_4$ independently are selected from hydrogen, $C_1$ to $C_8$ alkyl $C_1$ to $C_8$ alkoxy or $C_1$ to $C_8$ carboalkoxy, $C_6$ or $C_{10}$ aryl, selected from phenyl, 1-naphthyl and 2-naphthyl; halo, nitro, or $R_2$–$R_3$ or $R_3$–$R_4$ independently form an aromatic fused ring provided that $R_1$–$R_4$ are not all hydrogen and $R_3$–$R_4$ are not simultaneously methoxy when $R_1$ and $R_2$ are hydrogen; M is a pharmaceutically acceptable cation, $C_1$ to $C_{12}$ alkyl or acyl, or trialkylsilyl wherein the alkyl groups have from 1 to 6 carbon atoms.

23. A compound according to claim 22 wherein $R_4$ is methyl.

24. A compound according to claim 20 or 22 wherein $R_4$ is methyl.

25. A compound according to claim 21 or 22 wherein $R_4$ is methyl.

26. A compound of the formula:

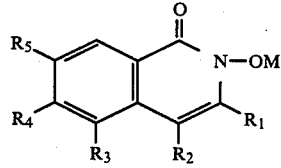

where $R_1$ is selected from $C_1$ to $C_4$ alkyl and $R_2$–$R_5$ independently are selected from hydrogen, $C_1$ to $C_8$ alkyl, $C_1$ to $C_8$ alkoxy or $C_1$ to $C_8$ carboalkoxy, $C_6$ or $C_{10}$ aryl, selected from phenyl, 1-naphthyl and 2-naphthyl; halo, nitro, or $R_3$–$R_4$ or $R_4$–$R_5$ independently form an aromatic fused ring, provided that $R_2$–$R_5$ are not all hydrogen and $R_5$ is nothydroxyl; M is a pharmaceutically acceptable cation, $C_1$ to $C_{12}$ alkyl or acyl, or trialkylsilyl wherein the alkyl groups have from 1 to 6 carbon atoms.

27. A compound according to claim 21 or 26 whrein $R_4$ is methyl.

28. A compound according to claim 21 or 26 wherein $R_4$ is methyl.

* * * * *

UNITED STATES PATENT AND TRADEMARK OFFICE
CERTIFICATE OF CORRECTION

PATENT NO. : 4,761,403

DATED : August 2, 1988

INVENTOR(S) : Bruce P. Gunn, James B. Summers, Jr.

It is certified that error appears in the above-identified patent and that said Letters Patent is hereby corrected as shown below:

Column 16, line 56: After "aromatic" and before "ring" insert --fused--

Column 18, line 19: Replace "nothydroxyl;" with --not hydroxyl;--

Signed and Sealed this

Twenty-first Day of August, 1990

*Attest:*

HARRY F. MANBECK, JR.

*Attesting Officer*      *Commissioner of Patents and Trademarks*